United States Patent [19]

Gatti et al.

[11] Patent Number: 5,098,531

[45] Date of Patent: Mar. 24, 1992

[54] ELECTROCHEMICAL SYNTHESIS OF 2-ARYL-HYDROQUINONES

[75] Inventors: Norberto Gatti, Galliate; Marco Foa, Novara, both of Italy

[73] Assignee: Istituto Guido Donegani S.p.A., Novara, Italy

[21] Appl. No.: 618,025

[22] Filed: Nov. 28, 1990

Related U.S. Application Data

[63] Continuation of Ser. No. 326,072, Mar. 20, 1989, abandoned.

[30] Foreign Application Priority Data

Mar. 24, 1988 [IT]  Italy ................................ 19944 A/88

[51] Int. Cl.$^5$ ............................................. C25B 3/02
[52] U.S. Cl. ............................................... 204/78
[58] Field of Search .................................... 204/78

[56] References Cited

U.S. PATENT DOCUMENTS

| | | | |
|---|---|---|---|
| 2,135,368 | 11/1938 | Vagenius et al. | 204/78 |
| 3,873,580 | 3/1975 | Rennie | 204/78 |
| 3,909,376 | 9/1975 | Degner | 204/78 |
| 4,071,429 | 1/1978 | Wagenknecht et al. | 204/78 |
| 4,159,365 | 6/1979 | Payet | 428/480 |
| 4,689,124 | 8/1987 | Noding | 204/78 |

*Primary Examiner*—John Niebling
*Assistant Examiner*—Steven P. Marquis
*Attorney, Agent, or Firm*—Morgan & Finnegan

[57] ABSTRACT

Preparation of 2-aryl-hydroquinones of formula (I) by oxidizing by an electrochemical route a compound of formula (II):

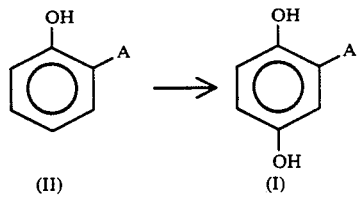

wherein A represents an aryl group optionally substituted with groups compatible with the reaction conditions in an acidic aqueous reaction medium, at temperatures within the range of from 10° to 100° C., and with anodes of graphite or $PbO_2$. The products are used in photography and in the field of liquid-crystal polymers.

22 Claims, No Drawings

ELECTROCHEMICAL SYNTHESIS OF 2-ARYL-HYDROQUINONES

This is a continuation of co-pending application Ser. No. 07/326,072, abandoned.

DESCRIPTION OF THE INVENTION

The present invention relates to a process for the electrochemical production of 2-aryl-hydroquinones by starting from 2-aryl-phenols.

More specifically, the present invention relates to the electrochemical oxidation of 2-aryl-phenols carried out in an electrochemical cell, in which the above compounds are subsequently reduced to 2-aryl-hydroquinones at the cathode.

The so-obtained aryl-hydroquinones are interesting intermediates for the synthesis of products applied in industry. More particularly, phenyl-hydroquinone is used in the industry as a monomer for the synthesis of liquid-crystal polymers (U.S. Pat. No. 4,159,365; U.S. Pat. No. 4,447,593; U.S. Pat. No. 4,600,765), and furthermore as a component of mixtures for photographic developers.

The preparation of 2-(aryl)-hydroquinones, by starting from the corresponding aromatic amines, via the diazo-salt, by arylation of benzoquinone and subsequent reduction of the so-obtained aryl-benzoquinones to the desired compound, is known [J.O.C. 4071 (1977)]. Such a process appears to be industrially burdensome owing to the large number of required steps; moreover, it uses potentially carcinogenic compounds, such as the aromatic amines.

The possibility of oxidizing 2-aryl-phenols to aryl-benzoquinones with hydrogen peroxide in the presence of ruthenium [Tetr. Lett. 5249 (1983)], with the possibility of obtaining the aryl-hydroquinone, by reducing the quinone, is also known. The yield reported for the 2-phenyl-quinone is quite low (20%).

In accordance with the present invention it has now been discovered that 2-aryl-hydroquinones may be obtained with high yields and high conversion rates, and with a good degree of purity, by starting from 2-aryl-phenols respectively having the formulae (I) and (II) as defined herein, by means of an electrochemical oxidation carried out in an aqueous solution containing a strong, non-oxidizing, mineral acid, preferably in the presence of an organic solvent, at a temperature within the range of from 10° to 100° C.

Therefore, an object of the present invention is a process for preparing 2-aryl-hydroquinones of formula (I):

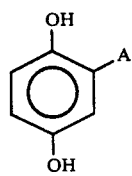

consisting or consisting essentially in subjecting to electrochemical oxidation 2-aryl phenols of formula (II):

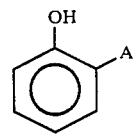

wherein A represents a $(C_6-C_{12})$-aryl radical, also possibly substituted with groups inert under the reaction conditions, in an aqueous solution containing a strong, non-oxidizing, mineral acid, preferably in the presence of an organic solvent at least partially miscible with the aqueous acidic solution, at a temperature within the range of from 10° to 100° C., according to the following reaction scheme

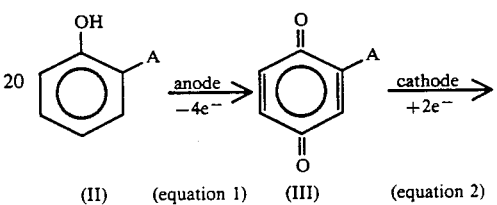

(II)    (equation 1)    (III)    (equation 2)

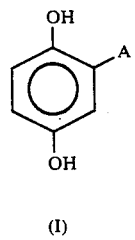

(I)

wherein the A symbol has the meaning indicated above.

As already stated, in the above formula (II) A represents a $(C_6-C_{12})$-aryl radical, possibly containing substituents consisting of groups inert under the operating conditions: particularly efficacious results are obtained by operating with substrates of formula (II) in which A is a phenyl radical (2-phenyl-phenol), a naphthyl radical (2-naphthyl-phenol), a diphenyl radical (2-diphenyl-phenol), and possibly substituted with one or more lower alkyl groups, halogen atoms, and so forth.

The process may be carried out in continuous or batchwise manner, and furthermore it may be carried out also in the absence of solvents. Still, according to the preferred form of practical embodiment thereof, the process is carried out by operating in an organic vehicle which is a solvent for the compound of formula (II). Acetonitrile, dimethylformamide, and, in general, dipolar aprotic solvents and their mixtures have been shown to be efficacious solvents.

The concentration of the reactant medium (II) may be within the range of from 0.1% to 20% by weight, and preferably from 0.5% to 10% by weight, although such values are not critical.

The reaction is preferably carried out as a single-step process inside a single-compartment electrochemical cell. As an alternative, the process may be carried out inside a conventional cell subdivided into two compartments, e.g., by means of a cationic membrane of Nafion ® (trademark for a product by the Dow Chemical Company) by operating in such a way that the anodic reaction and the cathodic reaction (equations 1 and 2 above) take place simultaneously inside both cell compartments.

Anodes are used which are made of graphite or PbO$_2$, with this latter being preferably electrodeposited, e.g., on graphite, on lead or lead alloys, or on titanium or on other "valve-metals" by which is meant metals giving rise to oxides having semiconductor properties.

These anodes may be substantially prepared by means of conventional methods.

The cathodic material used is not critical, and may be selected from among materials withstanding the involved process conditions such as, e.g., Pt, graphite, Pb and Pb alloys, stainless steel, Ni and Ni alloys, and Cu and Cu alloys.

When operating inside a single-compartment cell, maintaining in the electrolysis system an as-low-as-possible concentration of 2-aryl-benzoquinone is recommended, using, e.g., a suitable geometry of the cell having a cathodic surface which is equal to, and/or is larger than, the anodic surface, and/or maximizing the mass transport conditions.

In the oxidation reaction, current densities are used which are within the range of from 5 to about 1,000 mA/cm$^2$. The values of current density are preferably selected within the range of from 20 to about 500 mA/cm$^2$.

Conversion yields of the order of 90% and higher may be obtained according to the present invention.

The necessary amount of electrical charge is at least equal to the stoichiometric value of 4 F/mol of the converted product (II): normally, values within the range of from 4 to 12 F/mol of the converted product (II), according to the operating conditions (geometry of the cell, presence or not and type, of solvent, temperature, stirring, and so forth).

The reaction takes place in the presence of a strong mineral acid (also in admixture with an alkali-metal salt thereof selected from among the Na, K, Li salts, and so forth).

Such an acid is preferably selected from among sulphuric acid and phosphoric acid. Such an acid should not interact in any way in the process of oxidation of the 2-aryl-phenol (II). Furthermore, it is used in the form of an aqueous solution thereof.

The concentration, expressed as volumes of acid per each volume of the aqueous solution (v/v), is within the range of from 1% to about 10%.

The process is preferably carried out in the presence of a suitable organic solvent. As an alternative, it may also be carried out in the absence of such a solvent, provided that the substrate melts within the above-stated temperature range.

The ratio by volume of the acidic aqueous phase to the organic solvent may vary over wide limits; for example, the ratio may be within the range of from 0.05 to about 10 v/v.

The temperature at which the oxidation reaction is carried out is within the range of from 10° to about 100° C., and is preferably within the range of from 15° to about 70° C.

The concentration of compound (II) in the reaction mixture may vary over a wide range, e.g., from 0.1% to 20% by weight, and preferably from 0.5% to about 10%.

It is also possible to operate under condition of better constancy of the above said parameters, by gradually adding the compound (II) during the course of the reaction.

At the end of the oxidation, the reaction mixture may be treated according to known methods, e.g., it may be extracted with a solvent immiscible with water (e.g., methylene chloride or a hydrocarbon). This extract may be reduced with a suitable reducing agent (e.g., sodium metabisulphite in water, or SO$_2$), in order to convert into the desired reaction product (I) any possible traces of compound (III) which may still exist at the end of the electrolysis.

The product may then be recovered according to conventional techniques, such as, e.g., fractional distillation under reduced pressure, or by crystallization, or by column-chromatography.

The 2-aryl-phenol starting compounds (II) are per se known compounds and/or compounds which may be prepared according to well known methods; indeed, some of them are also available on the market (2-phenyl-phenol).

EXAMPLES

The present invention will now be disclosed in still more detail in the following examples, which are given for illustrative and not for limitative purposes.

EXAMPLE 1

To a single-compartment electrochemical cell containing a central anode of PbO$_2$ (electrodeposited on a titanium net), having a surface area of 32 cm$^2$, and two cathodes consisting of a nickel net (with a cathodic surface area of 60 cm$^2$), 3.38 g of 2-phenyl-phenol, 120 ml of acetonitrile, and 50 ml of an aqueous solution of sulphuric acid at 5% (v/v) are charged.

The electrolysis is carried out by feeding a constant current of 800 mA at the thermoregulated temperature of 50° C., with magnetic-drive stirring.

The electrolysis time is 5 hours and 25 minutes.

The reaction mixture is extracted with ethyl ether, washed with water, then washed twice with an aqueous solution of sodium metabisulphite, and dried over anhydrous sodium sulphate.

After the evaporation of the solvent, 3.83 g of a solid product, mainly constituted by phenyl-hydroquinone, is recovered. By crystallization from a toluene-hexane (70:30) blend, 3.07 g of phenyl-hydroquinone is obtained. The yield of crystallized product, computed with reference to reacted 2-phenyl-phenol, is 83%.

EXAMPLE 2

To the same electrochemical cell as in Example 1, 4.2 g of 2-phenyl-phenol, 120 ml of acetonitrile, and 50 ml of an aqueous solution of sulphuric acid at 5% are charged.

The electrolysis is carried out with a constant electrical current of 3.2 A for a time of 85 minutes, at a temperature of 50° C.

The reaction mixture is extracted, washed and dried in the same way as disclosed in Example 1, and is separated on a chromatographic column, with an eluent consisting of 60% of hexane and 40% of ethyl ether, 0.43 g of 2-phenyl-phenol and 3.27 g of phenyl-hydroquinone are obtained.

The yield of phenyl-hydroquinone, relative to the reacted 2-phenyl-phenol, is 79.3%.

The test was repeated with the addition of 12.2 g of 2phenyl-phenol, as 4 successive portions.

A total yield of 79%, as referred to reacted 2-phenyl-phenol, was obtained.

EXAMPLE 3

To the same electrochemical cell as disclosed in Example 1, 3.75 2 g of 2-phenyl-phenol, 120 ml of acetonitrile, and 50 ml of an aqueous solution of sulphuric acid at 5% are charged.

The electrolysis is carried out under the same conditions as disclosed in Example 1, but at a temperature of 15° C. for 6 hours and 40 minutes.

The reaction mixture is subsequently processed and is then separated in the same way as disclosed in Example 2.

227 mg of starting product and 2.60 g of phenyl-hydroquinone are obtained, with a yield of 67.4%.

EXAMPLE 4

To the same single-compartment electrochemical cell as disclosed in Example 1, 3.6 g of 2-phenyl-phenol and 160 ml of an aqueous solution of sulphuric acid at 5% (v/v) are charged.

The electrolysis is carried out at 70° C. with strong stirring, in order to produce an emulsion between the organic substrate and the aqueous phase. A constant current of 800 mA is fed for 8 hours and 20 minutes.

The reaction mixture is subsequently processed and separated in the same way as previously disclosed in Example 2.

0.70 g of the starting product and 0.63 g of phenyl-hydroquinone are recovered, with a yield of 20% relative to reacted 2-phenyl-phenol.

EXAMPLE 5

To a single-compartment electrochemical cell containing a central anode of $PbO_2$ (electrodeposited on a titanium net), having a surface area of 32 $cm^2$, and two cathodes consisting of a nickel net (with a cathodic surface area of 16 $cm^2$), 3 g of 2-phenyl-phenol, 66 ml of acetonitrile, and 30 ml of an aqueous solution containing sulphuric acid at 5% (v/v) are charged.

The electrolysis is carried out by feeding a constant current of 500 mA at the thermoregulated temperature of 30° C., with magnetic-drive stirring. The electrolysis time is 7 hours and 20 minutes.

The reaction mixture is extracted with ethyl ether, washed with water and extracted twice with ethyl ether, washed with water, and extracted twice with an aqueous solution of sodium metabisulphite, and is then dried over anhydrous sodium sulphate.

After the evaporation of the solvent, the separation is carried out on a chromatographic column, with the eluent being constituted by a hexane (60%)-ethyl ether (40%) blend. 266 mg of 2-phenyl-phenol and 2.70 g of phenyl-hydroquinone are recovered. The yield, computed relative to reacted 2-phenyl-phenol, is 90%.

EXAMPLE 6

To the same electrochemical cell as disclosed in Example 5, 2.7 g of 2-phenyl-phenol, 55 ml of acetonitrile, and 50 ml of an aqueous solution of sulphuric acid at 5% (v/v) are charged.

The electrolysis is carried out under the same conditions as disclosed in Example 5, for 7 hours.

The reaction mixture is subsequently processed and separated in the same way as previously disclosed in Example 5.

2.40 g of phenyl-hydroquinone is recovered, with a yield of 81.3%.

EXAMPLE 7

To the same electrochemical cell as disclosed in Example 5, 3.0 g of 2-phenyl-phenol, 75 ml of acetonitrile, and 25 ml of an aqueous solution of sulphuric acid at 5% are charged.

The electrolysis is carried out under the same conditions as disclosed in Example 5, but with the system being fed with a current of 800 mA for 5 hours.

The reaction mixture is subsequently processed and separated in the same way as previously disclosed in Example 5.

220 mg of the starting product and 2.27 g of phenyl-hydroquinone are recovered, with a yield of 74.7%.

EXAMPLE 8

To a single-compartment electrochemical cell containing a central anode of graphite having a surface area of 16 $cm^2$, and two cathodes consisting of a nickel net (with a cathodic surface area of 16 $cm^2$), 2.5 g of 2-phenyl-phenol, 90 ml of acetonitrile, and 30 ml of an aqueous solution containing sulphuric acid at 5% (v/v) are charged.

The electrolysis is carried out under the same conditions as disclosed in Example 5, over a time of 7 hours and 40 minutes.

The reaction mixture is subsequently processed and separated in the same way as previously disclosed in Example 5.

550 mg of the starting product and 1.34 g of phenyl-hydroquinone are recovered, with a yield of 63%.

EXAMPLE 9

In a double-compartment electrochemical cell with an anode constituted by a $PbO_2$ net having a surface area of $cm^2$, and a cathode of Pb with a surface area of 4 $cm^2$, and with the two compartments being separated by a porous-septum diaphragm, to the anodic compartment 1 g of 2-phenyl-phenol, 1 of acetonitrile, and 100 ml of an aqueous solution containing sulphuric acid at 5% (v/v) are charged. To the cathodic compartment, 20 ml of the same acidic aqueous solution and 5 ml of acetonitrile are charged.

The electrolysis is carried out at room temperature, with the electrical current being constantly maintained at the value of 400 mA, over a time of 6 hours The reaction mixture is then extracted with ethyl ether, and has a composition of 71% of phenyl-benzoquinone and 26% of starting product.

During a successive pass, phenyl-benzoquinone was quantitatively reduced to phenyl-hydroquinone inside the cathodic compartment.

EXAMPLE 10

To the same electrochemical cell as disclosed in Example 1, 3.45 g of 2-hydroxy-4'-methyl-diphenyl, 120 ml of acetonitrile, and 50 ml of an aqueous solution of sulphuric acid at 5% are charged.

The electrolysis is carried out with a constant electrical current of 1 A for a time of 4 hours and 10 minutes at a temperature of 60° C.

The reaction mixture is extracted, washed and dried in the same way as disclosed in Example 1, and separated on a chromatographic column with an eluent consisting of 60% of hexane and 40% of ethyl ether. 0.21 g of starting phenol and 2.28 g of 2,5-dihydroxy-4'-methyl-diphenyl are obtained.

The yield of hydroquinone derivative relative to the reacted starting product is 65%.

EXAMPLE 11

To the same electrochemical cell as disclosed in Example 1, 3.66 g of 2-hydroxy-4'-chloro-diphenyl, 120 ml of acetonitrile, and 50 ml of an aqueous solution of sulphuric acid at 5% are charged.

The electrolysis is carried out with a constant electrical current of 1 A for a time of 3 hours and 30 minutes at a temperature of 60° C.

The reaction mixture is extracted, washed and dried in the same way as disclosed in Example 1, and separated on a chromatographic column with an eluent consisting of 60% of hexane and 40% of ethyl ether. 0.24 g of unreacted phenol and 3.2 g of 2,5-dihydroxy-4'-chloro-diphenyl are obtained.

The yield of hydroquinone derivative relative to the reacted starting product is 88%.

EXAMPLE 12

To the same electrochemical cell as disclosed in Example 1, 1.70 g of 2-hydroxy-p-terphenyl, 120 ml of acetonitrile, and 50 ml of an aqueous solution of sulphuric acid at 5% are charged.

The electrolysis is carried out with a constant electrical current of 1 A for a time of 2 hours and 20 minutes at a temperature of 60° C.

The reaction mixture is extracted, washed and dried in the same way as disclosed in Example 1, and separated on a chromatographic column with an eluent consisting of 60% of hexane and 40% of ethyl ether. 0.33 g of starting phenol and 0.2 g of 2,5-dihydroxy-p-terphenyl are obtained.

The yield of hydroquinone derivative relative to the reacted starting product is 16%.

Although the invention has bene described in conjunction with specific embodiments, it is evident that many alternatives and variations will be apparent to those skilled in the art in light of the foregoing description. Accordingly, the invention is intended to embrace all of the alternatives and variations that fall within the spirit and scope of the appended claims. The above references are hereby incorporated by reference.

What is claimed is:

1. A single-step process for preparing 2-aryl-hydroquinones of formula (I):

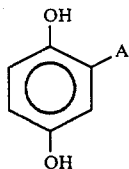
(I)

consisting in subjecting to an electrochemical oxidation 2-aryl-phenols of formula (II):

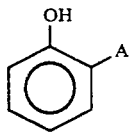
(II)

wherein A represents a $(C_6-C_{12})$-aryl radical, which may be substituted with groups inert under the electrochemical oxidation conditions, in an aqueous solution containing acetonitrile and a strong, non-oxidizing mineral acid, at a temperature within the range of from 10° to 100° C.

2. Process according to claim 1, wherein the aryl radical A is a group selected from the class consisting of phenyl, naphthyl, and biphenyl radicals.

3. Process according to claim 1, wherein the $(C_6-C_{12})$-aryl radical is substituted with at least one substituent selected from the class consisting of lower alkyl groups and halogen atoms.

4. Process according to claim 1, wherein the concentration of the compound (II) in the reaction mixture is within the range of from 0.1% to about 20% by weight.

5. Process according to claim 4, wherein the concentration of compound (II) in the reaction mixture is within the range of from 0.5% to about 10% by weight.

6. Process according to claim 1, wherein the process is carried out in an acidic aqueous solution containing a strong, non-oxidizing, mineral acid selected from the class consisting of sulphuric and phosphoric acids.

7. Process according to claim 6, wherein it is additionally carried out in the presence of an alkali-metal salt of the strong mineral acid selected from the class consisting of the salts of sodium, potassium and lithium.

8. Process according to claim 1, wherein said strong mineral acid is used in aqueous solution, at a concentration within the range of from 1% to about 10% by volume.

9. Process according to claim 1, wherein it is carried out at a volumetric ratio of the acidic aqueous phase relative to the organic solvent acetonitrile which is within the range of from 0.05 to about 10.

10. Process according to claim 1, wherein an electrical current density is used which is within the range of from 5 $mA/cm^2$ to about 1,000 $mA/cm^2$.

11. Process according to claim 10, wherein the electrical current density is within the range of from 20 to about 500 $mA/cm^2$.

12. Process according to claim 1, wherein it is carried out at a temperature within the range of from 10° to 100° C.

13. Process according to claim 12, wherein the temperature is within the range of from 15° to about 70° C.

14. Process according to claim 1, wherein the amount of electrical charge used in the electrochemical oxidation is at least equal to the stoichiometric value of 4 F/mol of product (II).

15. Process according to claim 14, wherein the electrical charge is within the range of from about 4 to 12 F/mol of product (II).

16. Process according to claim 1, wherein the oxidation reaction is carried out a single-step process, inside an electrochemical cell not subdivided into compartments.

17. Process according to claim 1, wherein it is carried out inside an electrochemical cell subdivided into two compartments.

18. Process according to claim 1, wherein an anode is used which is selected from the class consisting of graphite, lead and lead alloys, titanium and other valued metals.

19. Process according to claim 1, wherein a cathode is used which is selected from the class consisting of platinum, graphite, lead and lead alloys, stainless steel, nickel and nickel alloys, and copper and copper alloys.

20. Process according to claim 16, wherein the cathode surface is at least equal to the anode surface.

21. Process according to claim 1, the compound (II) is gradually added to the reaction mixture during the course of the reaction.

22. Process according to claim 1, wherein it is carried out either continuously or batchwise.

* * * * *